(12) United States Patent
Tomich et al.

(10) Patent No.: US 7,592,341 B2
(45) Date of Patent: Sep. 22, 2009

(54) PEPTIDE-ENHANCED CORNEAL DRUG DELIVERY

(75) Inventors: John M. Tomich, Manhattan, KS (US); Takeo Iwamoto, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 11/304,929

(22) Filed: Dec. 15, 2005

(65) Prior Publication Data

US 2008/0207623 A1    Aug. 28, 2008

Related U.S. Application Data

(60) Provisional application No. 60/636,437, filed on Dec. 15, 2004, provisional application No. 60/750,184, filed on Dec. 14, 2005.

(51) Int. Cl.
*A61K 47/16* (2006.01)

(52) U.S. Cl. .................. 514/249; 514/772.3; 514/773

(58) Field of Classification Search .................. None
See application file for complete search history.

(56) References Cited

U.S. PATENT DOCUMENTS 6,750,200 B1 *   6/2004   Tomich et al.  ................ 514/13

OTHER PUBLICATIONS

Broughman et al., Am. J. Physiol. Cell Physiol., 2004, vol. 286 (6), pp. 1312-1323.*

* cited by examiner

*Primary Examiner*—Christopher R. Tate
*Assistant Examiner*—Roy Teller
(74) *Attorney, Agent, or Firm*—Tracey S. Truitt; Polsinelli Shughart PC

(57) ABSTRACT

Improved methods and preparations are provided for ocular administration of therapeutic drugs. The preparations include respective quantities of a drug and a peptide which enhances transport of the drug across ocular tissues. The drug and peptide components may be separately administered or used as a mixture. The preferred peptide is NC-1059 (SEQ. ID NO. 1).

20 Claims, 14 Drawing Sheets

PEPTIDE-ENHANCED CORNEAL DRUG DELIVERY

CROSS REFERENCE TO RELATED APPLICATION

This application claims the benefit of U.S. Provisional Applications 60/636,437, filed Dec. 15, 2004 and 60/750,184, filed on Dec. 14, 2005; each of these provisional applications is incorporated by reference herein.

SEQUENCE LISTING

The present application contains a sequence listing in both paper and in computer readable format. The computer readable format is included on two compact discs, each containing an identical copy of 35702 Sequence Listing.ST25 having a size of 1 kb. The content of the computer readable compact discs are hereby incorporated by reference.

BACKGROUND OF THE INVENTION

1. Field of the Invention

The present invention is concerned with methods for ocular administration of drugs and drug preparations for this purpose. More particularly, the invention is concerned with such methods and preparations including one or more selected drugs and a peptide serving to enhance the transport of the drug(s) across ocular tissues. The preparations may also include other ingredients such as a buffer and an acrylic polymer.

2. Description of the Prior Art

Ocular conditions such as glaucoma, ocular inflammations and infections often require ocular administration of drugs for most efficient treatment. This stems from the poor accessibility of a number of ocular regions to systemic circulation and the resultant fact that the administered drugs are poorly retained in the ocular regions. Unfortunately, drug transport across the cornea is inefficient, owing to the fact that the intrinsic conjunctional epithehlia forms tight junctions with high resistance to ocular delivery. Moreover tear washout and the blinking reflex dilutes and washes out the administered drugs.

These factors contribute to intra-ocular bioavailability of generally less than 10% for drugs. Consequently, this low efficiency necessitates the use of high concentrations of the active ingredients in the ophthalmic formulations. Furthermore, the ocular barrier tissues are highly sensitive to high local concentrations of drugs or vehicles. Generally, lipophilic molecules show the best intrinsic permeation rates across the cornea. However, many therapeutically important compounds such as antibiotics are more polar and hydrophilic molecules, and are thus poorly transported across the corneal epithelium.

The treatment of bacterial keratitis, an ocular infection of the corneal stroma, exemplifies the problems associated with ocular administration of drugs. This condition is reported in approximately 30,000 cases annually in the United States (including bacteria, fungus, and acanthamceba). Gram-negative *Pseudomonas* species and gram-positive *Staphylococci* and *Streptococci* strains are the most frequently identified pathogenic organisms. While less severe forms of bacterial keratitis may not lead to corneal scarring and sight loss, most cases are at risk for subsequent loss of vision. Untreated corneal infections may result in corneal perforation, with the potential for development of endophthalmitis and loss of the eye. Rapid diagnosis and timely therapeutic intervention are essential because ocular destruction can occur rapidly, within 24 hours with highly virulent organisms. The appearance of antibiotic resistant bacterial strains requires an increasing use of more exotic antimicrobials, many of which are highly polar in character and therefore poorly transported across epithelia.

Many ophthalmic medications are formulated for instillation as eye drops. The obvious accessibility of the front of the eye belies the difficulty of efficiently delivering certain classes of drugs across the outer epithelial layer. Further considerations are the small volume (30 µL) that can be delivered to the eye and rapid clearance observed in these tissues. Low bioavailability of drugs from eye drops is mainly due to tear production, low absorption, low residence time, and the impermeability of corneal epithelium. These factors severely limit the effectiveness of this route of administration. Various formulations have been developed to increase and maintain drug concentrations prior to transport. One approach has been the addition of viscose polymers such as the poly (acrylic acid) derivatives Carbopol 1342P NF, Carbopol 974P and Carbopol 980 NF. These additives increase contact time with the eye. Another emerging approach is the use of therapeutic contact lenses wherein several different hydrogel materials are presoaked in different ophthalmic drugs. These lenses are then tested for drug uptake and delivery.

The barrier function of epithelial cells is performed by tight junctions in the form of complex, highly regulated, protein structures. Transient openings of these junctions are required for a variety of bodily functions including sperm maturation, extravasation of lymphocytes across endothelia and nutrient uptake associated with activity of the Na+/glucose transporter. The cytoskeleton of actin microfilaments, associated with myosin and other cellular proteins, maintains the morphology of epithelial cells. An intracellular ring of actin and myosin at the apical/lateral interface (the perijunctional actomyosin ring) provides a scaffold for the tight junctions between epithelial or endothelial cells. The primary transmembrane structural components of tight junctions are the claudin family proteins, junctionall adhesion molecules (JAM) and occluden. These proteins interact directly with the ZO family proteins, which link them to the perijunctional ring of the cytoskeleton. These proteins interact with several regulatory/signaling molecules. The ZO proteins contain a guanylate kinase (GUK) domain as well as a src homology 3 (SH3) domain and a PDZ domain. The atypical PKC isotype specific interacting protein (ASIP) and the ras binding protein AF-6 also contain PDZ domains, and have been shown to associate with junctional complexes. PKC phosphorylates occluden, which results in its translocation to the tight junction. In subconfluent epithelial cell cultures, ZO-1 localizes to the nucleus but is located at the junctions in confluent cultures of epithelial cells. Myosin light chain kincase phosphorylation of the myosin II (regulatory subunit) is associated with contraction of the perijunctional ring and increases in paracellular permeability. Protein kinase A (PKA) activation increases conductance, but not permeability to large molecules across tight junctions, while activation of PKC increases paracellular permeability. Barrier function of the tight junction is also affected by calcium levels, which maybe under the control of PKC. Rho GTPase family members control organization of the actin cytoskeleton, (specifically cdc42). Rab GTPase proteins, which play a regulatory role in vesicular trafficking, such as rab13 and rab3b, appear to play a role in junctional regulation that remains undefined. These observations demonstrate that numerous cellular components might be targeted to modulate the paracellular conductance.

Endothelial tight junctions also share many components with epithelial tight junctions although distinct extracellular modulators impinge on their function. A variety of techniques are currently being investigated to selectively and transiently circumvent the barrier function of epithelia and endothelia. For example, pharmaceuticals are being linked to actively transported peptides as a means to cross the blood-brain barrier. While this allows very selective targeting, the method requires a unique synthetic process for every transported compound. Alternatively, methods are being developed to reduce epithelial tight junctions enough to allow large molecules to diffuse to the interstitial space. Both calcium chelators and surfactants have been employed, but have unacceptable side effects including global changes in cell function and diminished cell adhesion. Alternatively, the zonula occludens toxin of *Vibrio cholerae* (ZOT) provides a naturally occurring alternative for increasing the permeability of small intestine epithelia. ZOT and its eukaryotic homologue, zonulin, interact with an epithelial membrane receptor that leads to a reduction in epithelial resistance, presumably by activation of PKCa. The effects of ZOT are rapid in onset (<20 minutes) and readily reversible upon washout. Thus ZOT is an excellent candidate as an adjunct to standard therapy to increase oral bioavailability of large molecules. In fact, ZOT has been used to increase the permeation of anticonvulsant drugs across epithelial monolayers, to increase the uptake of PEG 4000 from rabbit small intestine and into the bloodstream, and to reversibly increase intestinal permeability to insulin and immunoglobulins. In diabetic rats, the bioavailability of oral insulin was sufficient to control blood glucose to the same degree as parenteral administration. However, ZOT has some drawbacks as a more generalized therapeutic in that it is a large peptide (399 a.a.) and has a relatively small therapeutic target. Effects are observed only in the small intestine where distinct receptors are present. It was recently reported that an 8 a.a. peptide could fully inhibit the effects of ZOT on small intestine.

Synthetic peptides based upon portions of naturally occurring proteins have been employed as epithelial ion channels for a number of years. In addition to developing potential therapeutics for cystic fibrosis, these synthetic channel-forming peptides have greatly expanded the understanding of channel structure. The M2 segments of both the acetylcholine receptor delta subunit and the glycine receptor alpha subunit have been employed. In each case, ion selective channels were produced. Amphipathic transmembrane α-helices are thought to be the structural motif responsible for formation of the aqueous-facing pore region of ion channels. The M2GlyR peptide has single-channel conductances of 25 pS and 49 pS with open lifetimes in the millisecond time. These observations are in good agreement with single-channel properties described for glycine receptor conductance measured in inside-out patches from cultured rat spinal cord neurons. Lysine residues have been added to either terminus of the M2GlyR peptide ($NK_4$-M2GlyR, $CK_4$-M2GlyR) to increase their aqueous solubility. Two-dimensional total coherence spectroscopy (TOCSY-NMR) and reverse phase HPLC studies revealed that peptides became less aggregated in aqueous solution as the number of positively charged amino acids at the termini was increased. The ability of $CK_4$-M2GlyR and other M2GlyR peptides to induce apical chloride secretion from monolayers of Manin-Darby canine kidney cells (MDCK) was determined by measuring peptide-induced increases in ion transport. $NK_4$-M2GlyR and CK4-M2GlyR applied to the apical membrane of human epithelial cell monolayers induced transepithelial Cl⁻ and fluid secretion, although with differing potency.

The eye has been described as an immune privileged site where immunity is suppressed. Corneal allograft transplants appear tolerated rather than rejected like solid organ transplants such as heart, lung, pancreas, bowel, kidney and skin. This immune suppression is hypothesized to occur as a result of the absence of both vascular and lymphatic systems. There is also an anterior chamber-associated immune deviation (ACAID) that is characterized by a suppression of some forms of systemic immunity after the administration of antigen into the eye. A number of reports have shown that cytokines such as IL-2, IL-4, IL-12, or granulocyte macrophage-colony stimulating factor secreted from neural derived tumors generate anti tumor immunity.

A literature survey reveals that there are no references dealing specifically with corneal immuno/inflammatory responses upon topical application of synthetic peptides. There are studies that describe experimental autoimmune encephalomyelitis (EAE) and associated anterior uveitis (AU) induced in lab animals with the systemic exposure of different peptides sequences derived from myelin basic protein (MBP), HLA-B, interphotoreceptor retinoid-binding protein (IRBP), and fragments from the human S-Antigen (S-Ag).

While the eye's reduced immunological potential appears to make this tissue a candidate for peptide-based therapeutics, full-blown immune responses are known. Responses have been seen in connection with corneal allografts and herpes simplex infections. Herpetic corneal stromal keratitis (HSK) is a T cell-controlled, immunoinflammatory lesion resulting from Herpes simplex virus infection. Release of proinflammatory molecules such as IL-1 has been implicated in HSK pathogenesis. Recent results suggest that early treatment with IL-1 receptor antagonist (IL-1 ra) protein reduces the severity of HSK. Other bacterial infections, such as those caused by *Staphylococcus aureus* and *Pseudomonas aeruginosa* can also lead to immuno/inflammatory responses.

When an immune response is triggered a number of cellular events mediate the corneal immuno/inflammatory response. These include activation and migration of local antigen-presenting cells (APCs), including Langerhans cells (LCs), up-regulation in pleiotropic proinflammatory cytokines such as interleukin-1 (IL-1) and tumor necrosis factor-α (TNF-α) that can mediate a wide array of immune functions in addition to up-regulating protease expression. Additionally, chemokines attract both non antigen-specific inflammatory cells such as neutrophils and CD4+ T helper type 1 (Th1) cells that mediate most of the destruction in the cornea. It has been shown that the cornea is a potent producer of nitric oxide (NO) a molecule that is toxic to various pathogens and possesses immunomodulatory properties. The production of various cytokines, including interleukin (IL)-1, IL-6, IL-8, IL-18, interferon (IFN)-γ and TGF-β, has also been demonstrated in cultured corneal cells in vitro. Both dependent and independent class II transactivator (CIITA) pathways of MHC class II expression have been found in the eye and the brain.

While the eye may be an immune privileged tissue, tears produced by the eye's lachrymal glands do not remain in the eye. Tiny ducts, which line both eyelids and the inner edges of the eyelids, drain the constantly produced tear fluid from the surface of the eyes into the nasal cavity and throat. The nasal and oral cavities are predominantly lined with epithelial cells that show both innate and active immune responses. Both systemic and local immune responses can be generated through the immunization process. The innate response involves the local secretion of defense proteins that are uniquely expressed in the mouth, nose and upper airways.

The active immune response of nasal epithelia is well known and has been successfully exploited for the delivery of vaccine antigens against a variety of infectious agents including influenza, human respiratory syncytial virus (RSV), meningococcal OpaB and OpaJ proteins, and equine herpesvirus-1 (EHV-1).

Specific peptide-induced active immunity with nasal exposure has been seen for several sequences. These responses include Th2-type T cell, cytotoxic T-cell and neutralizing antibody responses. An immunization strategy against Alzheimer's disease was examined using Abeta 1-15 or full-length Abeta 1-40/42 with the mucosal adjuvants, native labile enterotoxin (LT) or its non-toxic form, LT(R192G). Mice were immunized against the intestinal nematode *Trichinella spiralis* by intranasal administration of a 30-mer peptide, residues 210 to 239, from the *T. spiralis* 43-kDa antigen.

Immuno suppression and tolerance have also been induced with the administration of soluble protein/peptide antigens to the oral and nasal mucosa. The effects of experimental autoimmune neuritis (EAN), an animal model of the human Guillain-Barre syndrome (GBS) were attenuated after nasal administration of the neuritogenic peptide 180-199 and of the cryptic peptide 56-71 of the rat neuritogenic P0 protein of peripheral nerve myelin. Synthetic peptides corresponding to T- or CD4(+) epitopes of the acetylcholine receptor (ACHR) protein have prevented experimental myasthenia gravis (EMG) in mice.

The broad spectrum of immunological and inflammatory responses of the eye and ocular epithelium pose a significant problem in the effective treatment of ocular conditions that remain largely unresolved. Accordingly, what is needed in the art is a method of and compositions for reversibly modifying epithelial tight junctions so as to permit absorption or transport of drugs or other desirable compounds that are either presented from passage or that have decreased passing efficiency across epithelial cell layers. What is further needed is a method or composition that decreases the amount of drug or other desirable compound needed to treat conditions and/or infections of tissues protected by tight junctions. What is still further needed is a method or composition that can reversibly modify epithelial tight junctions without damaging or injuring the epithelial cells forming the tight junctions. Finally, what is further needed is methods of and compositions for decreasing transepithelial resistance in increasing ion transport across epithelial cells regulated by tight junctions.

SUMMARY OF THE INVENTION

The present invention overcomes the problems outlined above and provides improved methods and preparations for administration to ocular tissues. Broadly speaking, the methods of the invention comprise contacting epithelial tissue (preferably corneal or conjunctiva-sclera) with one or more therapeutic drugs and a peptide for increasing the transport of the drug through the tissue, as compared with transport of the drug in the absence of the peptide. It is theorized that the presence of the peptide serves to open paracellular pathways and reversibly modify the tight junctions in the epithelial tissue, thereby facilitating drug transfer.

The preparations may be in the form of mixtures in a carrier, or the drug(s) and peptide may be separately administered. In the latter case, the drug(s) and peptide may be substantially simultaneously administered or alternately within about 2 hours of each other, even if peptide is washed from the tissue after a certain amount of incubation or contact time.

In preferred forms, the peptide is selected from the group consisting of Seq. ID No. 1, Seq. ID No. 2, derivatives thereof, and mixtures thereof. Seq. ID No. 1 is a previously known peptide, NC-1059. Generally, the useable peptides should have a molecular weight of from about 2721-3000. Where drugs/peptide mixtures are employed, the peptide should normally be present at a level of from about 50-500 µM, and more preferably from about 100-300 µM. The mixtures may include an aqueous carrier, as well as additional ingredients such as a buffer and/or an acrylic polymer.

A wide variety of drugs may be used in the methods and preparations of the invention. Generally, drugs or bioactive polymers having molecular weights up to at least 70,000 but not greater than 1,500,000 can be used following peptide administration as described herein. Such administration will permit these drugs to traverse epithelial tight junctions across the paracellular pathway, after peptide administration. Exemplary drugs are selected from the group consisting of Emidine, Patanol, Azopt, Ciloxan, Travatan, Aldox, Icaps, Scipro, Hc Otic, Lunigan, Ocu Flox, Cosopt, Timoptic, Allergan's Alphagan, vancomycin, penicillin, dexamethazone, methotrexate, ascorbic acid, benzylpenecillin, tamoxifen, dextran, polymyxin B, BIDPY-vancomycin, neomycin, and mixtures thereof. Where drugs/peptide mixtures are used, the drug(s) should be present at a level of from about 0.05-1000 µM, more preferably from about 0.25-500 µM. However, those of skill in the art will be able to determine the amounts of drug necessary to confer the desired result.

Usually, the compositions of the invention are administered by contacting in vivo human epithelial tissue, preferably ocular tissue, with the composition, although if desired ex vivo administration can be carried out. The present invention will also find utility in other epithelial tissues and cell lines including mammalian epithelial cell lines, IPEC-J2 (porcine-jejunum), T-84 (human colon), Calu-3 (human airway), PVD 9902 (porcine vas deferens), MDCK, SV40-immortalized human corneal epithelial cells (THCE), and the 10.014 p RSV-T multilayered human corneal cell line.

Peptides in accordance with the invention may also be modified without a consequent loss of their functionality. For purposes of the present invention, these modifications will be considered to be within the definitions of SEQ ID NOS. 1 and 2. Examples of modifications covered by the definitions of SEQ ID NOS. 1 and 2 include the epsilon amino group of the four lysines transformed by the addition of 1) Fmoc-8-amino-3,6-dioxyaoctanoic acide (Fmoc-$NHCH_2CH_2OCH_2CH_2OCH_2COOH_2$), 2) Trichloroacetic acid ($Cl_3CCOOH$), 3) glycosylated with Na-(Fmoc)-3-O-(2-acetamido-3,4,6-triacetyl 1-2-deoxy-α-D-galactopyranosyl)-L-serine (see below) or 4) formylate to make the carboxyamide. Each of these compounds is commercially available and can be added directly to the lysines of NC-1059 during solid-phase synthesis using standard Fmoc-chemistries. All of these derivatives are modified in the final product to block any residual amino groups and at the same time, deprotect all of the OH-groups. These modifications increase the hydrophillicity of the peptide while eliminating the positive charges of the lysines.

The Fmoc-8-amino-3,6-dioxyaoctanoic acid is simply a very short polyethylene glycol (PEG3) derivative. The trichloracetic acid and PEG3 treatments will also reduce the antigenicy of the peptide, thereby reducing the changes for an antibody being raised against the exposed N-terminus of the peptide. The complete mono-glycosylation of the lysines may produce a hapten and potentially increase antigenicity.

DETAILED DESCRIPTION OF THE PREFERRED EMBODIMENT

Figure 1:
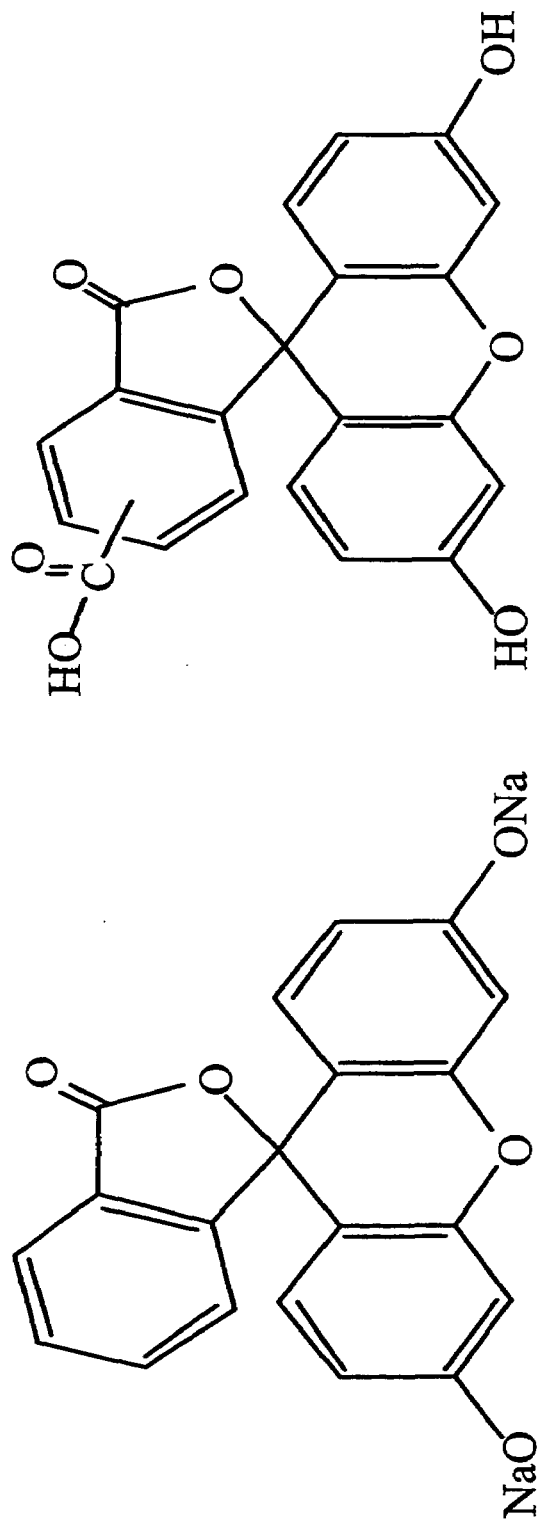
FIG. 1 illustrates the chemical structure of two fluorescent dyes used in ex vivo transcorneal transport experiments as described in Example 1.

The following examples set forth preferred techniques in accordance with the invention. It is to be understood, however, that these examples are provided by way of illustration and nothing therein should be taken as a limitation upon the overall scope of the invention.

Example 1

Peptide Synthesis

The two peptides tested (NC-1059, Seq. ID No. 1 and NC-1063, Seq. ID No. 2) were synthesized by solid phase synthesis using 9-fluorenyl methoxycarbonyl (FMOC) chemistry on an ABI 431A peptide synthesizer (Perkin-Elmer Biosystems, Norwalk, Conn.). Reagents included p-Hydroxymethylphenoxymethyl (HMP) resin reloaded with the C-terminal amino acid (Perkin-Elmer) and $N^{\alpha}$-Fmoc; amino acids (Perkin-Elmer, Bachem (Torrence, Calif.), Peninsula Laboratories (Belmont, Calif.) and Peptides International (Louisville, Ky.)). Coupling reactions were performed in the presence of a ten-fold excess of amino acid with HOBt: HBTU in dimethylformamide (DMF). The peptide was released from the resin and all side chain protecting groups were removed via a chemical cleavage reaction using trifluoroacetic acid (TFA) in the presence of 0.5 mL of 1,2-ethanedithiol and 0.5 mL of thioanisole at room temperature for 200 min. The cleaved peptide was washed with ether and the resultant precipitate was dried in vacuo. Crude peptides were purified to homogeneity by reversed-phase high performance liquid chromatography (RP-HPLC) using a polystyrene based-$C_4$ semi-prep RP-HPLC column (PLRP-S 300 Å, 7.5×50 mm Polymer Laboratories, Amherst Mass.). The column was equilibrated with 18% acetonitrile ($CH_3CN$) in deionized-distilled water containing 0.1% TFA at a flow rate of 2.0 mL/min. After maintaining the 18% acetonitrile for 3 min post sample injection, a programmed gradient from 18% $CH_3CN$ to 54% $CH_3CN$ over 10 minutes was then executed. The desired product eluted at about 40.5% $CH_3CN$.

The purified peptide was characterized by mass analysis using both MALDI-TOF mass spectrometry and sequenced using ESI-Ion trap mass spectrometry. These techniques confirmed that the peptide was assembled correctly and that all protecting groups were removed.

Epithelial Monolayer Experiments

These experiments were conducted in the manner described by Broughman et al., *Am J Physiol Cell Physiol* 280: C451-8, 2001, and Broughman et al., *Biochemistry*, 41:7350-8, 2002, both incorporated by reference herein. Briefly, channel-forming activities of the M2GlyR analogs were assessed by incubating the desired peptide concentrations with MDCK monolayers (Grantham et al., *Trans Assoc Am Physicians*, 102:158-62 1989, incorporated by reference herein) grown on permeable supports (Snapwell, 12 mm dia.; Costar Corp; ref. 31). MDCK monolayers were placed in modified Using chambers containing 5 mL of Ringer's solution in the apical and basolateral compartments. Short circuit current ($I_{sc}$), transepithelial potential ($V_{te}$) and transepithelial resistance ($R_{te}$) were monitored prior to and throughout peptide exposure. The unmodified M2GlyR and other less soluble sequences were dissolved in dimethyl sulfoxide (DMSO) because of the reduced solubility of these peptides in aqueous solutions. The maximal final concentration of DMSO, 0.1%, was without effect on $I_{sc}$. More soluble forms of M2GlyR analogs were prepared as 1.0 mM stocks in Ringer's solution. In inhibitor experiments, either basolateral bumetanide (100 μM) or selected channel blockers (e.g., DASU-02, $CdCl_2$, DPC, IAA-94, DNDS, and $CFTR_{Inh}$-172) were added after $I_{sc}$ reached a steady state in the presence of the peptide.

Stastical Analysis

Transepithelial conductance was determined using selected, well-defined conditions (e.g., in the presence of selected concentrations of the synthetic peptides and at distinct time points). Four observations were made in each condition depending upon the observed variation. For presentation, the arithmetic mean and standard error of the means were presented. For concentration dependencies, all observations (not just the means which would inappropriately weight the data set) were employed in a user-defined curve-fitting routine (Sigmaplot, SPSS). A modified Hill equation of the form '$y=A*(x^n/(k_{1/2}{}^n+x^n))+B$' was used where y is the observed conductance, A is the maximal conductance, x is the concentration of peptide, k is the concentration of peptide for a half maximal response ($k_{1/2}$), n is the Hill coefficient, and B is the minimal conductance. B should not vary between data sets because it is the basal value. However, the predicted value of B was used as a test of the curve-fitting routine. The value of n takes on a similar value in all conditions. Therefore, the first equation for each data set was fit with no constraints. The constraint of n allowed for a straightforward interpretation of the other derived parameters, $k_{1/2}$ and A. Comparisons of $k_{1/2}$ and A were then used to determine the treatment effects of magnitude and potency of the overall response. Analysis of absolute conductance values was then conducted without transformation. Analysis of 'fold changes' in conductance were conducted following a square root transformation of the data to normalize the distribution of the data set.

Eye Transport Assays

1. Isolation of corneas for transport assays

For rabbit in vitro studies, corneas were obtained from eyes of New Zealand White rabbits weighing 5.0 to 5.5 kg, which were anesthetized and then killed by intracardiac injection of sodium pentobarbital (97.2 mg/kg). All animal protocols conformed to the Guiding Principles in the Care and Use of Animals (Department of Health, Education and Welfare Publication, NIH 80-23) and he ARVO Resolution for the Use of Animals in Ophthalmic and Vision Research. For a given pair of eyes, the epithelium was scraped from one of the corneas with a scalpel blade; on the opposite eye the epithelium was left intact. The corneas were excised from the globes with a 2-mm scleral rim and mounted on corneal rings that had been modified according to the method of Dikstein et al., *Isr J Med Sci.* 8(8):1523-8 1972, incorporated by reference herein. This method prevented trauma to the corneal epithelium and distortion of the corneal curvature during clamping in the acrylic-block perfusion system. The scleral rim serves as a gasket and permits the cornea to be suspended within the corneal ring.

2. Permeability Assays in Isolated Rabbit Cornea

The retina and pigment epithelium were removed and the cornea was clamped in the corneal holder. The exposed surface area for diffusion was 1.2 cm² for the cornea and 1.1 cm² for the sclera. The perfusion chamber was made of acrylic and placed in a water jacket to maintain the temperature of the cornea and perfusion medium at 35° C. A volume of 6 mL of balanced salt solution with oxidized glutathione (BBS Plus, Alcon Laboratories Inc, Fort Worth, Tex.) at pH 7.4 was placed in the endothelial chamber. The peptides were added to the balanced salt solution with oxidized glutathione at a concentration of 1 mM. Six milliliters of each solution was added to the epithelial chamber. Constant mixing of the reservoir solution was achieved with an airlift siphon gassed with 95% air-5% carbon dioxide to maintain a pH of 7.6. Serial 0.5-mL samples were removed from each reservoir at 30-minute intervals, and after three hours at the termination of the permeability study, the remaining 3 mL was removed. Each tissue sample was analyzed for drug use by the method of Maren et al (The transcorneal permeability of sulfonamide carbonic anhydrase inhibitors and their effect on aqueous humor secretion; 36 *Exp Eye Res;* 457-479 (1983), incorporated by reference herein). The rate of appearance of drug (micromolar per hour) divided by the concentration in the epithelial chamber yielded a first-order rate constant ($k_{in}$) for each drug, as follows: $k_{in}$=(micromolar per hour in endothelial solution)/micromolar of epithelial solution. The corneal permeability (P) was obtained by taking into account the volume (6 mL) of the endothelial chamber and the corneal area (square centimeters), as follows: P=$k_{in}$ endothelial chamber volume/corneal area.

3. Confocal Studies

Whole eyes were removed within 15 minutes of death, washed with BBS-plus and fixed for 24 hr at 4° C. in fixative containing 2% paraformaldehyde and 0.2% glutaraldehyde in BBS-plus. The fixed tissues were cross-sectioned by vibratome into 100 micron sections and fixed again for another 24 hr in the same fixative. A laser scanning confocal microscope was used for the florescent dye conjugated drug localization studies. Tissues were routinely preincubated with 50 mM glycine in BBS-plus for 10 min to quench free aldehydes introduced during fixation. Dye transfer was evaluated by examining the tissue sections under the confocal microscope. For quantification, the extent of dye transport was determined by visualizing the fixed dye molecules within the different ocular tissues at 4× magnification for whole eye slices and 60× for specific regions of interest. Images were loaded into Adobe Photoshop 6.0, changing the index color to grey scale. The pixels were then counted using Scion Image (Scion Image, Inc., Frederick, Md.).

4. Tissue Studies

Figure 2:
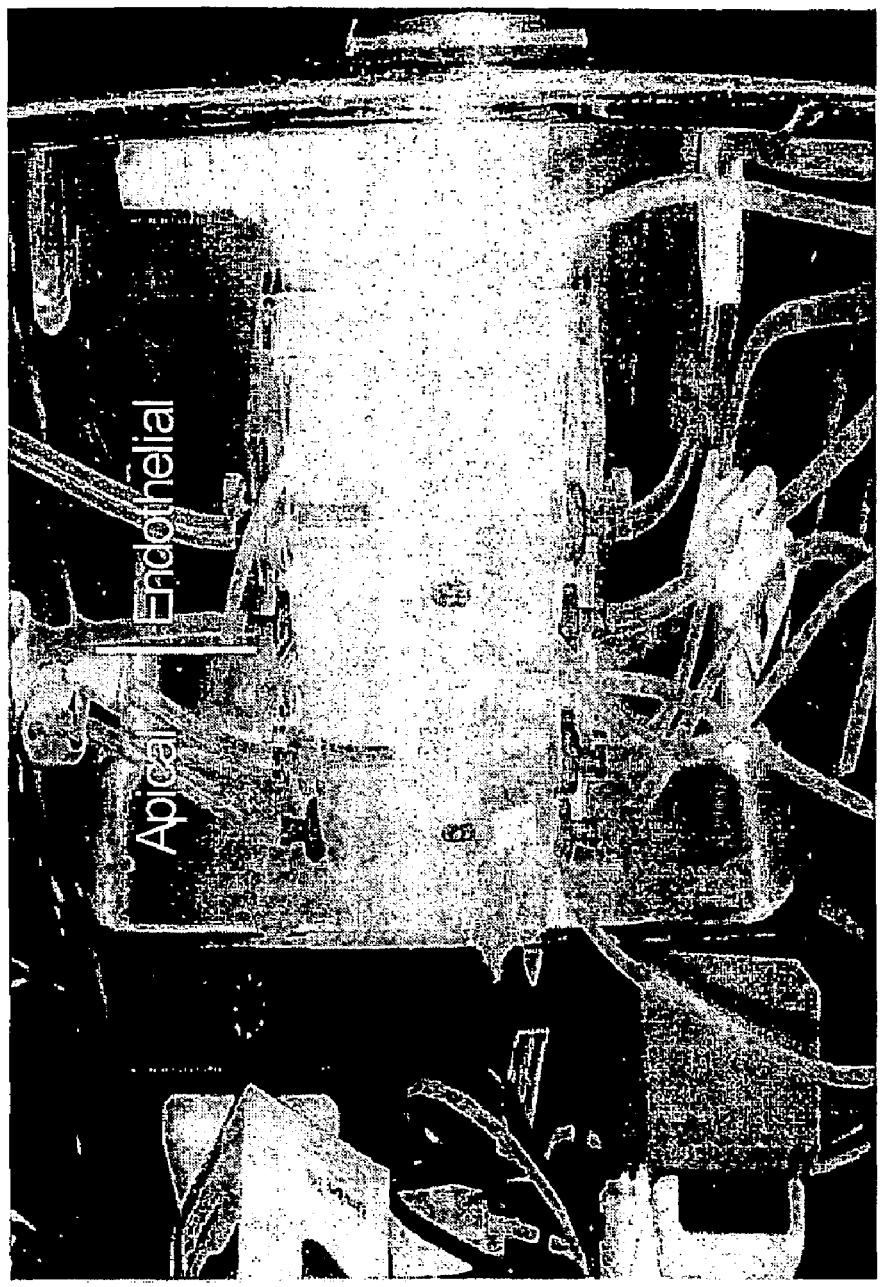
FIG. 2 is a photograph illustrating the corneal mounting chamber used in the transport experiments.

In order to optimize the transport assay described above, two different dyes, Sodium Carboxy Fluorescein (NaF) and 5(6)-Carboxy Fluorescein (CF), (FIG. 1) were used. The sodium compound has been shown in previous studies to enter corneal epithelium directly through the apical membrane and move transcellularly. The carboxy-derivative however cannot pass directly through the membrane, only passing between the cells via the paracellular pathway. Numerous paired sets of experiments were conducted using each of the two dyes. The paired experiments included a control cornea obtained from one of the eyes of a rabbit, which was bathed in the BSS+ buffer and given 100 μL of water at the start of the experiment. In the test cornea, from the second eye of the same rabbit, 100 μL of peptide was added at time zero to produce a 150-200 μM peptide solution in BSS+. Both the water and the peptide additions were made on the apical surface of the cornea. After 20-30 minutes of incubation, dye was added to the apical bathing solution (final concentration 300 μM of dye) and allowed to remain in contact with the cornea for 6 hours. The preincubation with the peptide is preferred for the peptide to fully open the tight junctions. At 30-minute intervals, 75-100 μL aliquots were removed from the endothelial bathing chamber and the concentration of the transported dye determined. In some later experiments the corneal surfaces were rinsed 2-3 times with fresh BSS+ (wash out) to remove unbound peptide prior to the addition of the dye. A photograph illustrating a pair of corneal mounting chambers is set forth in FIG. 2. The peptide is added to the apical bathing chamber. In this figure, dye is also present in the apical chamber. Minor frothing of the added test peptide can be seen in the upper chamber. In these experiments the added peptide should reversibly open the tight junctions of the surface epithelial layer and allow the dye to enter via the paracellular pathway into the tissues of the eye. In the dye experiments two measurements are made: total transport across all of the corneal layers and dye trapped within the corneal layers at the end of the six-hour incubation.

Figure 3A:
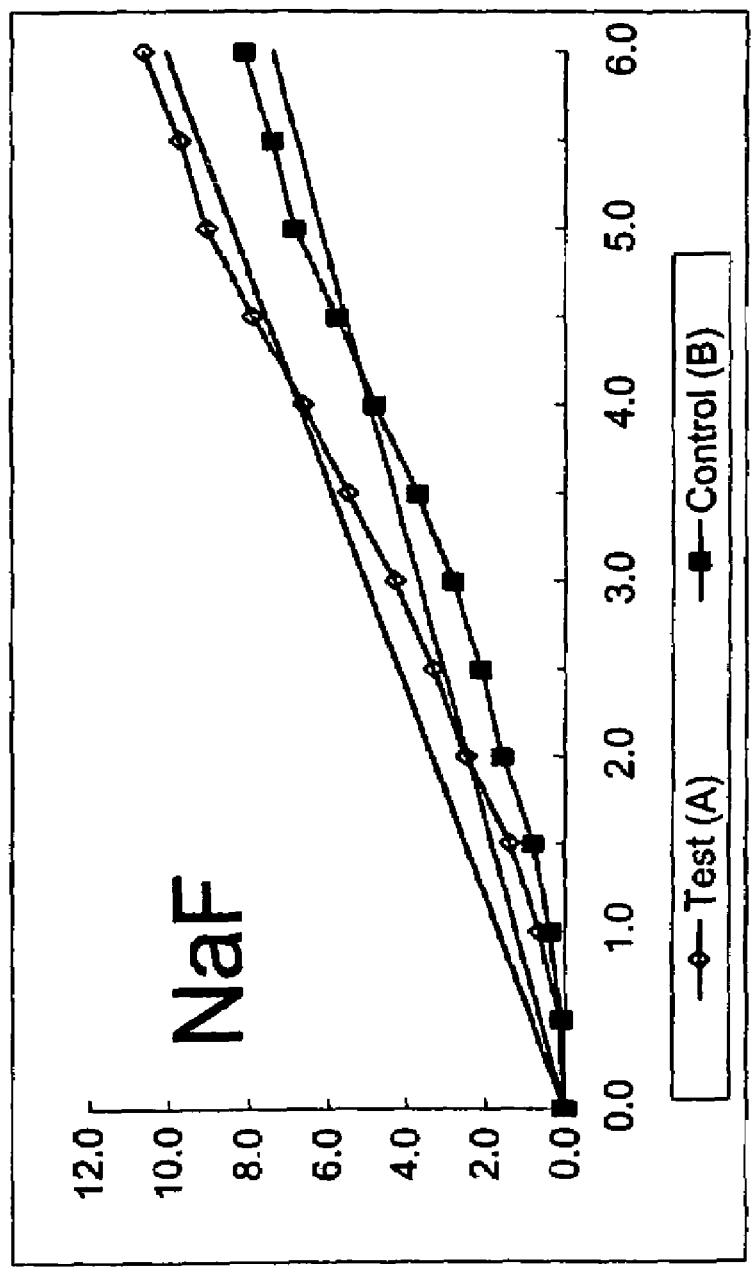
FIG. 3A is a graph of transported NaF vs. time for the transcorneal transport experiment of Example 1, using NaF plus peptide (Test A) and NaF alone (control Test B)

The following Figs illustrate the transcorneal transport rates of the two dyes. In FIG. 3A NaF was tested after a 30 minutes preincubation with NC-1059 followed by peptide washout with BSS+. This dye is hydrophobic enough to normally move transcellularly. This being the case, NaF does not require the test peptide to facilitate its transcorneal movement. However, this Fig. clearly illustrates that the peptide enhances delivery above that seen with the dye alone.

Enhanced dye uptake after the washout is an important observation because it shows that the permeabilizing effect of the peptide does not require its continual presence. Another important observation is the duration of the transport enhancement. If the peptide had a short duration of action one might expect an initial burst for the test sample that would offset the two curves and at later times the curves would be parallel with identical slopes of the lines. In FIG. 3A, they clearly have different slopes.

When the peptide and dye are co incubated, reduced transport is observed indicating that NaF and NC-1059 interact directly. In fact, the solution containing both compounds becomes cloudy and a colored precipitate forms. The peptide and dye concentrations are close, 200 and 300 μM, respectively, and peptide of this length could have multiple binding sites. Peptides/proteins have long been recognized for their ability to bind dyes. Quantitative isothermal calorimetry was used to study the binding of NaF and CF.

Figure 3B:
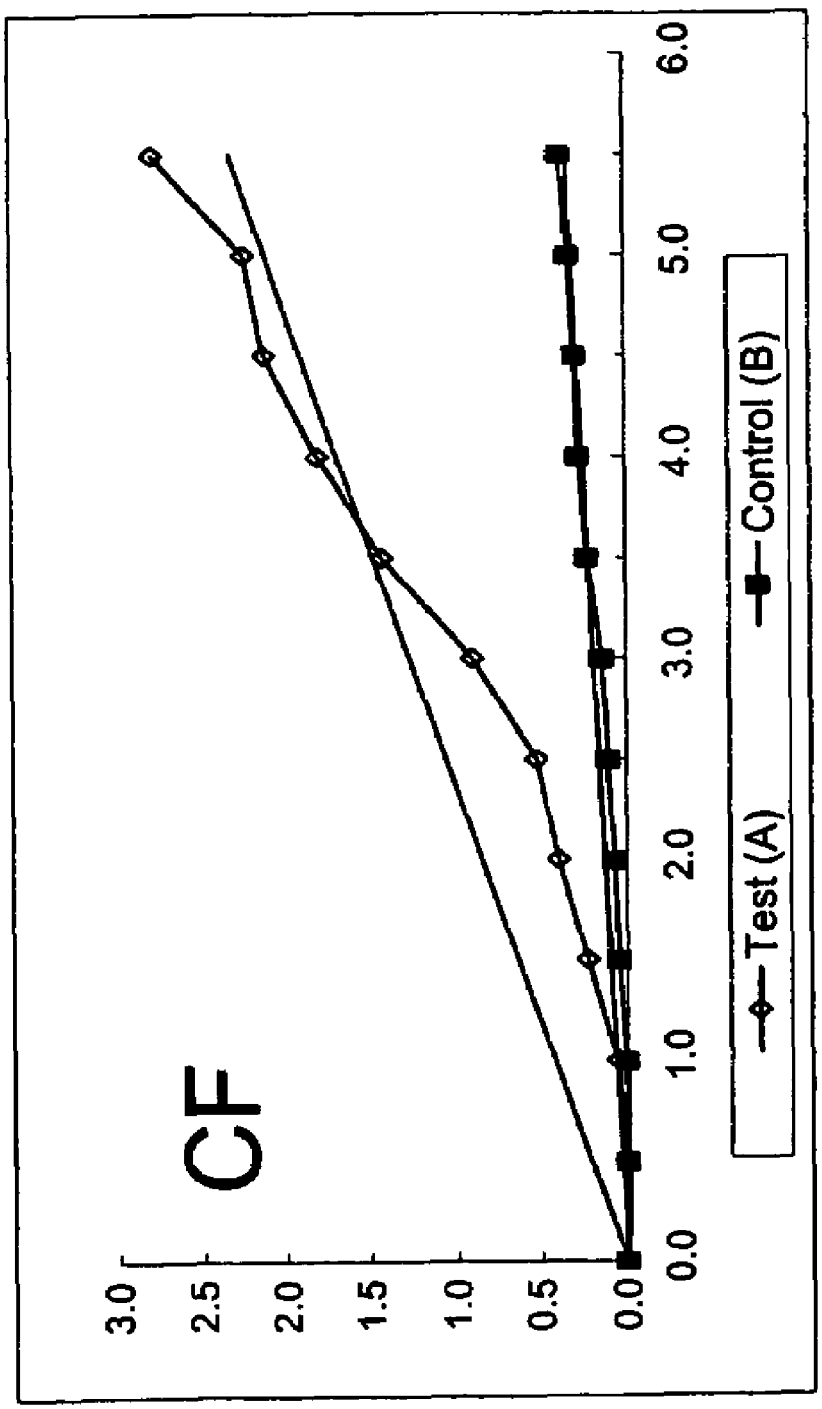
FIG. 3B is a graph of transported CF vs. time for the transcorneal transport experiment of Example 1, using CF plus peptide (Test A) and CF alone (control Test B)
Figure 3C:
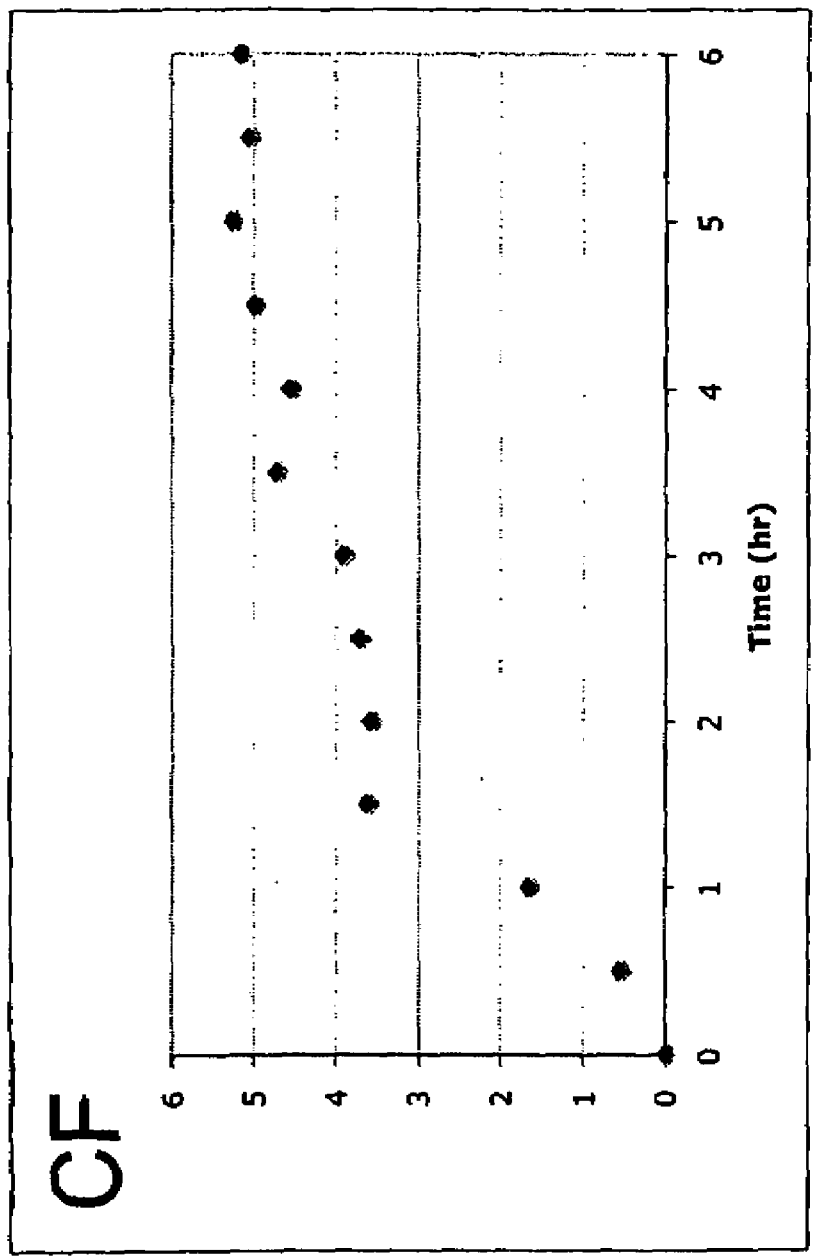
FIG. 3C is a graph summarizing three separate experiments performed with co-incubation of CF and peptide as described in Example 1.

In contrast when the more hydrophilic carboxyfluorescein (CF) is used, FIG. 3B, a very different result is seen. Co-incubation of the peptide and the dye does not cause precipitation and shows (after the 30 min preincubation with the peptide) a dramatic increase in dye transport for the test cornea over that seen for the control cornea. This increase is on the order of 7.4-fold in this experiment. As mentioned above it is well known that CF cannot move transcellularly, only paracellularly. This dye represents a better model for hydrophilic drugs that show little ability to cross the barrier epithelial layer of the cornea. In FIG. 3C the results from three separate experiments performed with co-incubation of the dye and peptide are summarized. Here the fold difference at each sampling point is calculated (net transport for test/net transport for control). An average increase in amount of material transferred in the presence of the peptide is about 5-fold. The shape of the curve suggests that the rate of transfer reaches a maximum at about 4.5-5.0 h. Error bars have been omitted for clarity, but the standard deviation is ±1.0-1.5 fold. In contrast with the NaF dye, this dye does not appear to interact significantly with the peptide. The duration of action for the peptides exceeds the time interval of the assay. Also removal of soluble peptide after the 30 min preincubation does not stop the stop the higher dye transport rates. The observed lag seen for the appearance of dye in the endothelial chamber most likely reflects the slow rate of diffusion of the dye across the multi layered corneal tissue.

Figure 3D:
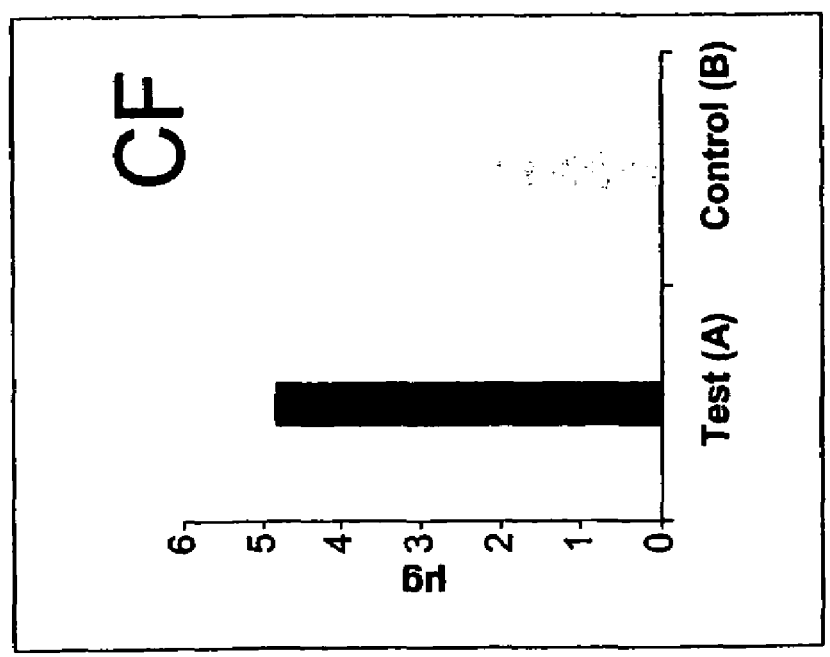
FIG. 3D is a bar graph setting forth the corneal uptake of CF plus peptide (Test A) and CF alone (control Test B) in the transcorneal transport experiment of Example 1.
Figure 3E:
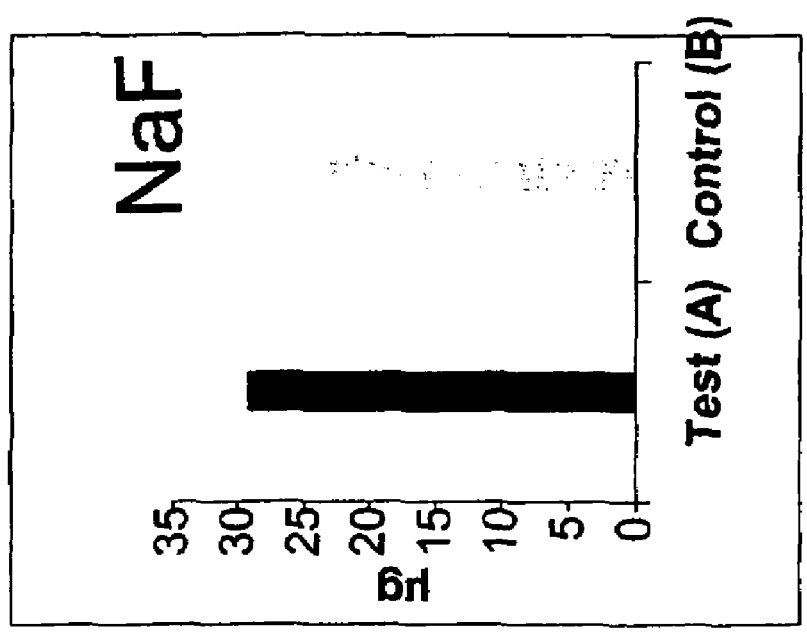
FIG. 3E is a bar graph setting forth the corneal uptake of NaF plus peptide (Test A) and NaF alone (control Test B) in the transcorneal transport experiment of Example 1.

At the end of all the corneal translocation assays, the corneas are washed and then checked for internalized dye. This value gives an indication of corneal uptake and retention of small molecules. Representative values for the two different dyes are shown in FIGS. 3D and 3E. While the gross amounts of dye remaining in the two experiments are quite different, there is a net increase in retained material using either dye in the presence of the test peptide. The net differences are substantively different depending on the intrinsic ease of access for the dyes to the issue. The NaF, which enters the cornea rather easily, shows only a net increase of 27% in the presence of the peptide, while CF, which is taken up poorly, shows a 234% increase over control. This result strongly indicates that the peptide can significantly enhance the uptake of small hydrophilic molecules into the cornea.

When the incubation time was increased to 2 h for NC-1059 (Seq. ID No. 1), prior to the addition of the dye, no detectable increase in CF transport was observed. Both the control and test transport rates were identical. This result shows that within 2 hours of peptide exposure, the tight junctions have opened and then resealed. This observation is remarkable for several reasons: up to this point the reversibility of the peptide induced resistance loss in vitro was demonstrated. In this in situ experiment, the transient nature of this peptide's effect on opening the paracellular pathway is clearly in evidence. The restoration of the barrier function of the cultured epithelial monolayers required a longer time period (6 hours) before resistance begins to return. Another salient observation in the in situ experiments is that in the absence of the dye, the paracellular pathway opens and closes within 2 hours while in the presence of the dye and peptide (FIGS. 3A, 3B) transport rates continue to increase for the full duration of the experiment. This result suggests that the presence of the dye within the paracellular pathway may have an inhibitory effect on closure of the tight junctions. Since the tight junctions are formed by the dimerization of the claudins, occuldins, etc., the binding of dyes to these proteinaceous elements could prevent the required protein-protein interactions from resealing.

Figure 4A:
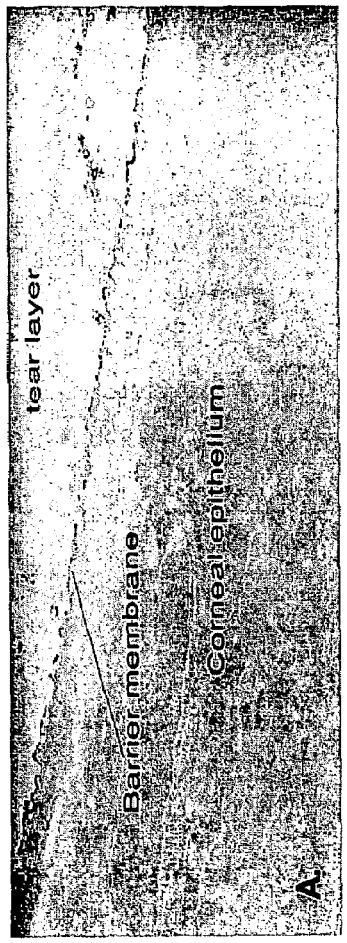
FIG. 4A is a 12000× transmission electron micrograph (TEM) photograph illustrating the control untreated cornea in the transcorneal transport experiment of Example 1.
Figure 4B:
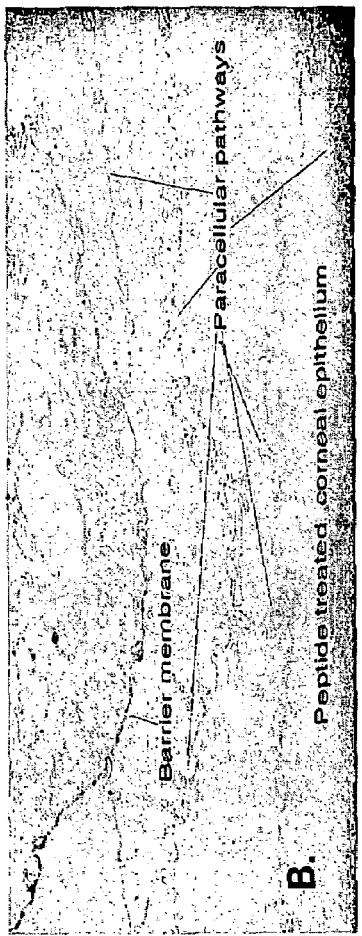
FIG. 4B is a TEM similar to that of FIG. 4A, but illustrating a NC-1059 (Seq. ID No. 1) peptide-treated cornea.
Figure 4C:
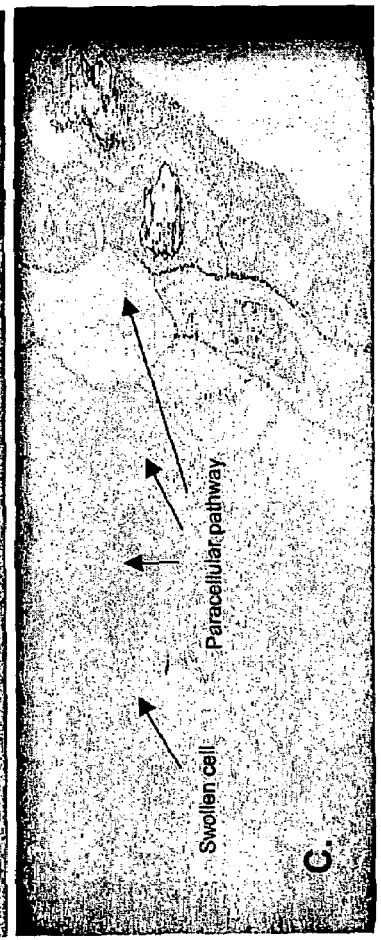
FIG. 4C is a TEM similar to that of FIG. 4A, but illustrating a cornea treated with ruthenium red dye.
Figure 5A:
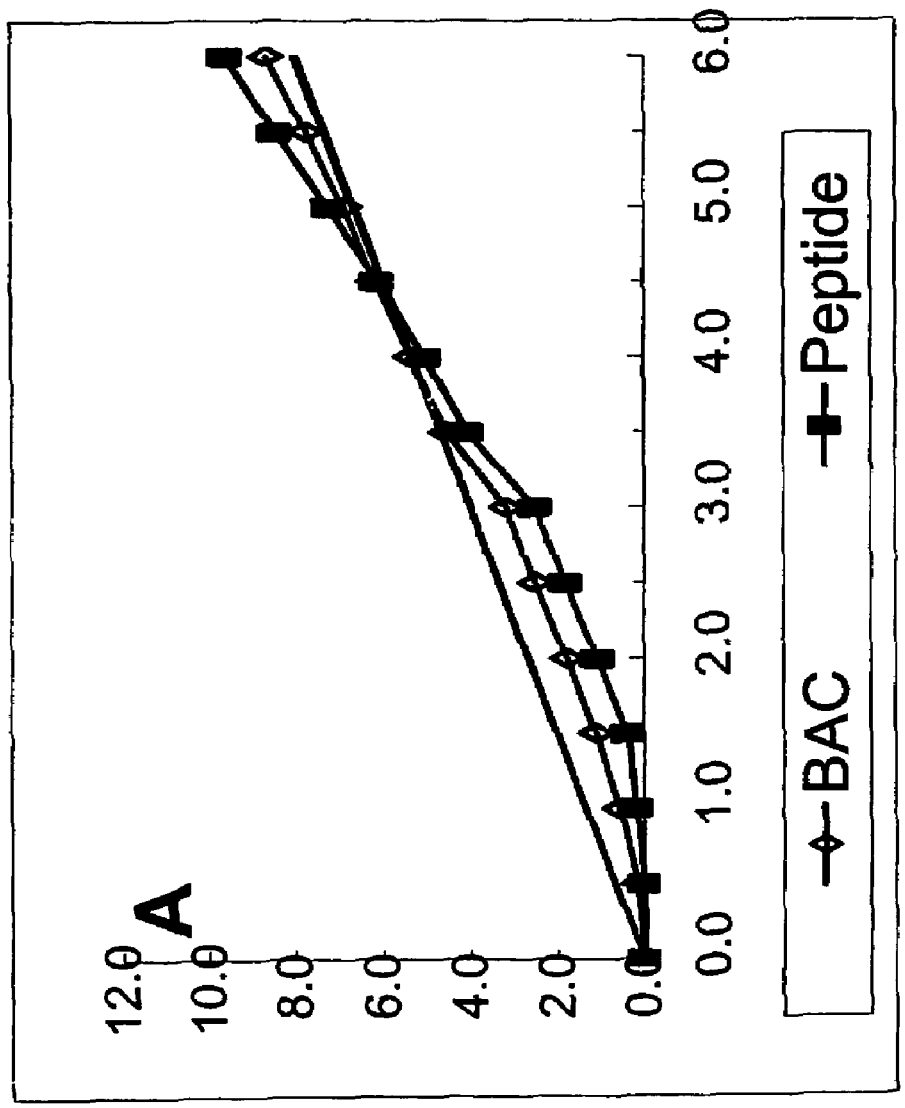
FIG. 5A is a graph of transported CF vs. time using a 15 minute preincubated mixture of CF and NC-1059 (Seq. ID No. 1) peptide (peptide Test) and a control (BAC)
Figure 5B:
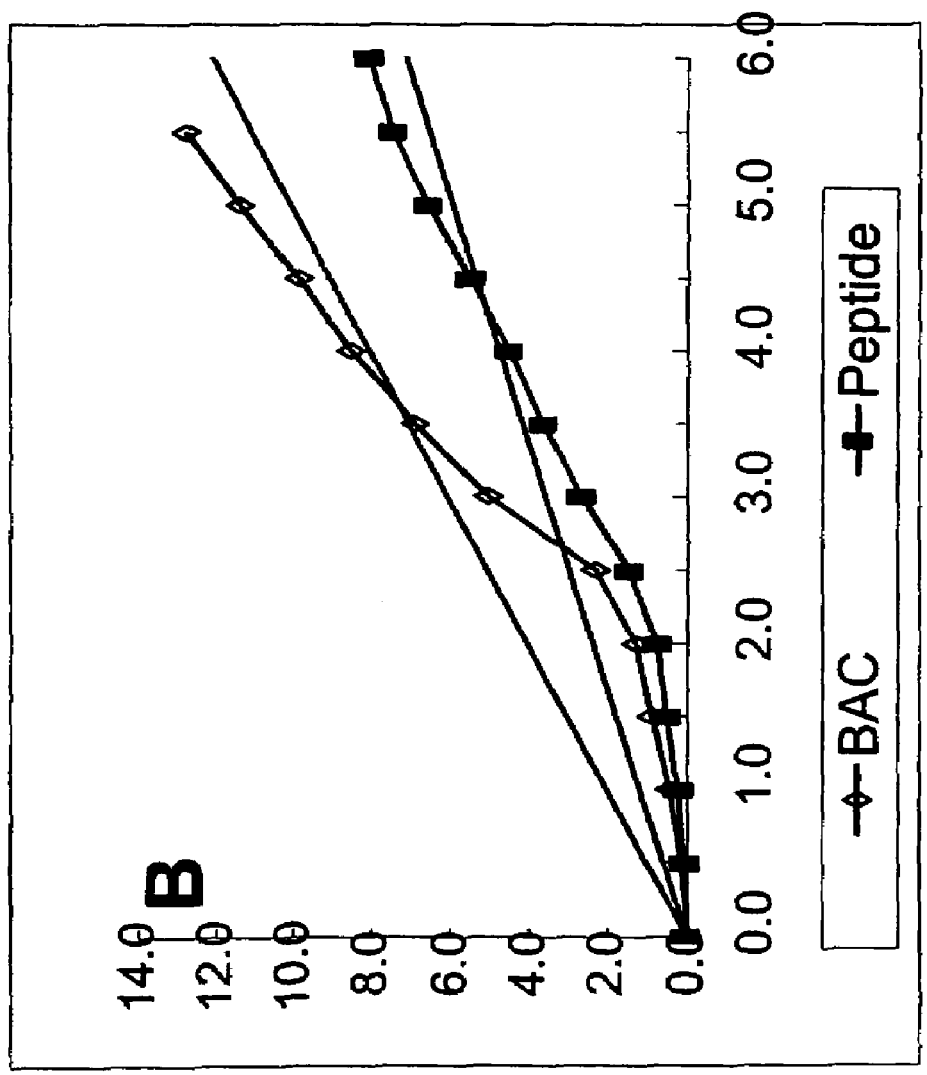
FIG. 5B is a graph of transported CF vs. time using a 30 minute preincubated mixture of CF and NC-1059 (Seq. ID No. 1) peptide (peptide Test) and a control (BAC)
Figure 6:
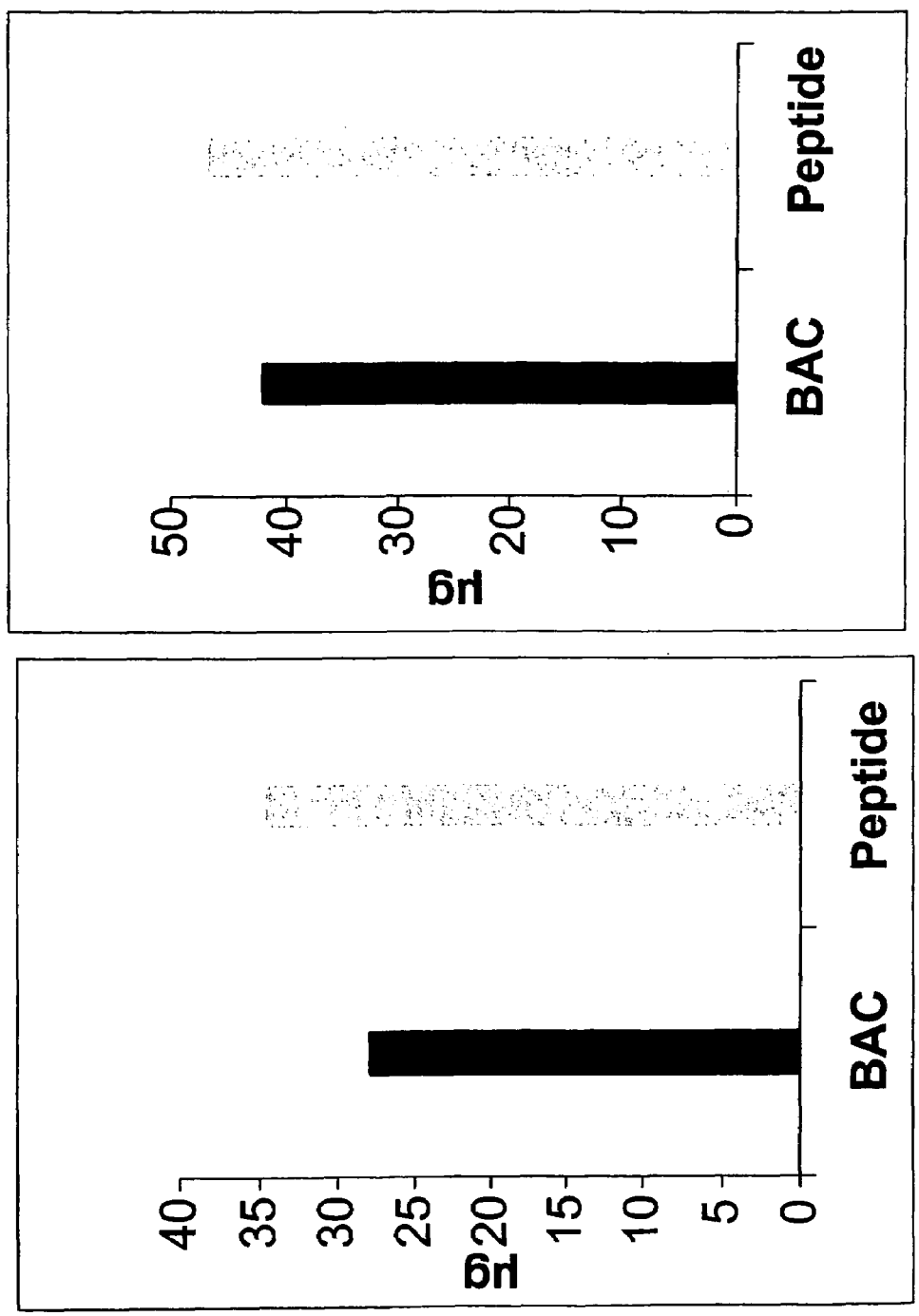
FIG. 6 is a series of bar graphs illustrating the residual CF values obtained from the 15 minute and 30 minute preincubation tests of FIGS. 5A and 5B.

In order to document the in situ opening of the tight junctions, peptide treated corneas were chemically fixed at the end of a dye transport assay for morphology studies. The control and test samples were treated with the dye ruthenium red, which binds to the plasma membrane of epithelium and cannot pass the tight junctions. The electron micrographs prepared are shown in FIG. 4. In the peptide treated tissue, the multilayered epithelium is apparent due to the binding of the ruthenium red which now has access to the paracellular pathway. The morphology of the cells is unaltered suggesting that the opening of the junctions is biochemical rather than mechanical as would be expected with agents that cause the cells to swell or shrink. As a control, the ophthalmic preservative benzalkonium chloride (BAC) was used in place of the peptide. BAC is known to disrupt the corneal epithelium barrier function and cause cellular damage at concentrations greater than 0.005%. Severe disruption of surface cell layers occurred simultaneously with decreased resistance. NC-1059 (Seq. ID No. 1) was compared to BAC in a paired cornea experiment: 0.01% BAC solution and 200 μM ml of the peptide were incubated individually for either 15 or 30 minutes in the test chambers. The solutions were washed. 5 mL of BSS plus was added to both chambers and then spiked with 2 mL of CF. Sample aliquots were taken (100 μL) every half hour from the endothelial chamber for 6 hours. The results for the two different preincubation times followed by washing are shown in FIG. 5. With 15 min of preincubation (5A) the induced transport rates for CF in the paired corneas appear identical for BAC and NC-1059 (Seq. ID No. 1). With a longer preincubation time, 30 minutes (5B), however the BAC begins to promote increased CF translocation after the three-hour test point. At the end of the experiment treated corneas were tested for residual internalized CF and then fixed for morphological analysis by EM. The residual CF data is shown in FIG. 6. The peptide showed 34 and 42 μg of CF for the 15 and 30 min incubations, respectively. The BAC showed 27.8 and 40.7 μg of CF for the 15 and 30 min incubations, respectively. Both treatment methods produced similar uptake amounts, within experimental error. Increased preincubation exposure time for the test compounds did increase the overall amount of delivered dye. An EM study using ruthenium red to highlight the plasma membrane and grid staining to increase the contrast was performed on the 30 minute samples used to generate FIG. 5. A dramatic difference is observed in the way these two test compounds altered corneal epithelial morphology and integrity (FIG. 4). The peptide treated cells (A), with the exception of the sloughing cell showed normal healthy epithelial morphology such as that shown in FIG. 4. The ruthenium red was able to stain down 3-4 layers of quite multilayered corneal epithelium.

The BAC treated cells (B) showed an altered morphology with some cells appearing swollen. This is consistent with the damaged morphologies described by others. The ruthenium red was able to stain down 4-5 layers with the BAC. The deeper penetration of the ruthenium red with the BAC treated tissues could explain the higher transport rates observed in FIG. 5. NC-1059 (Seq. ID No. 1) and BAC show similar abilities to open tight junctions but only NC-1059 (Seq. ID No. 1) is able to accomplish this without altering the normal morphology of the corneal epithelium.

Figure 7:
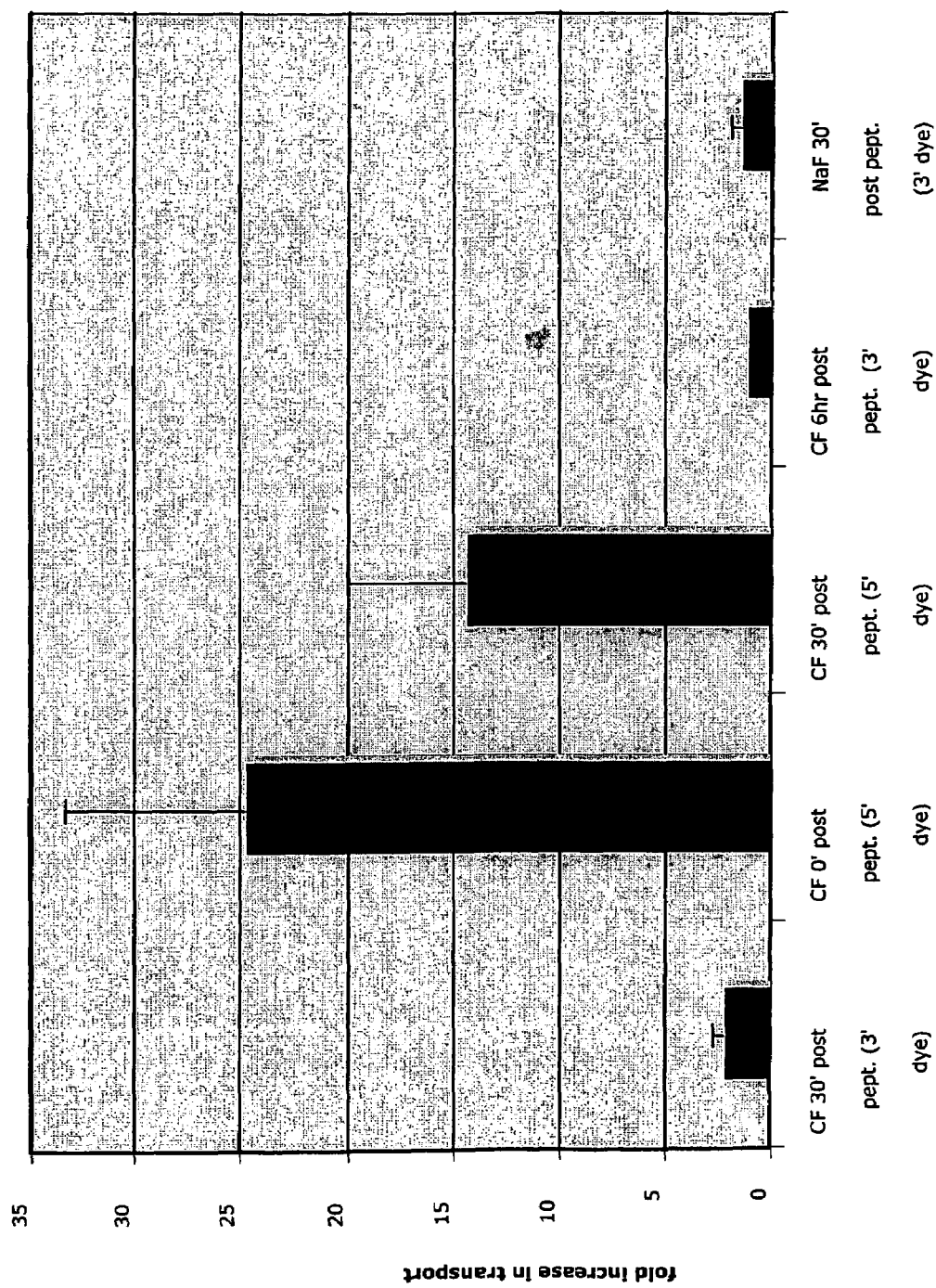
FIG. 7 is a bar graph illustrating the fold changes observed between peptide-treated and untreated eyes, as described in Example 1.

A series of in vivo corneal epithelial permeability experiments in unanaesthetized rabbits was also conducted. NC-1059 (Seq. ID No. 1) was prepared in BSS (200 µM) and placed inside the lower eyelid of one eye with the other eye receiving an equal amount of BSS alone. The solutions were held in place for 3 minutes and then washed with BSS. After the indicated incubation periods, both eyes received 300 µM NaF or CF and the dye was kept in place for 3 or 5 minutes. After the contact period the eyes were washed with 40 mL of BSS solution. Total uptake was measured for both the control and treated eyes with an OcuMetrics, Ocular Fluorophotometer. The fold changes between the peptide treated and untreated eyes were calculated (FIG. 7). The peptide treatment followed by a 3 min exposure to the dye resulted in a 2.2±0.46 (n=3) fold increase. With the 5 minute treatment of CF added at 0 and 30 minutes after the rinse resulted in 24.7±8.6 (n=3) and 14.4±5.6 (n=2) fold increases, respectively. These results show that the peptide was able to open tight junctions in vivo in hand held animals. Also these results showed that increasing the exposure time of the dye, in peptide treated eyes, significantly increases corneal uptake. It would also appear that adding the dye immediately after peptide exposure results in the highest permeation. In the fourth column, the eyes that were previously monitored at the 30-minute time point (showing a 2.7-fold increase) were challenged a second time with CF at 6 hours, and showed only a 1.1-fold increase. The reduced uptake at the 6-hour time point documents the transient effects of the peptide in vivo. This transient effect has been observed under all assay conditions: in vitro, in situ and in vivo. In the final column, the fold increase is only 1.7±1.1 (n=2). Viewed alone, this fold increase is some-what misleading because the net amount of more hydrophobic NaF taken up in eyes is higher (7.8-fold) than with the CF dye.

The in vivo studies, while limited to a single peptide concentration and a single peptide exposure time, do appear to indicate that the peptide is capable of opening the tight junction in a transitory manner. Increasing contact time with the hydrophilic dye correlates directly with increased permeation. These results suggest that it should be advantageous to employ one of the Carbopol resins in the final formulation of the drug to increase contact time.

Figure 8:
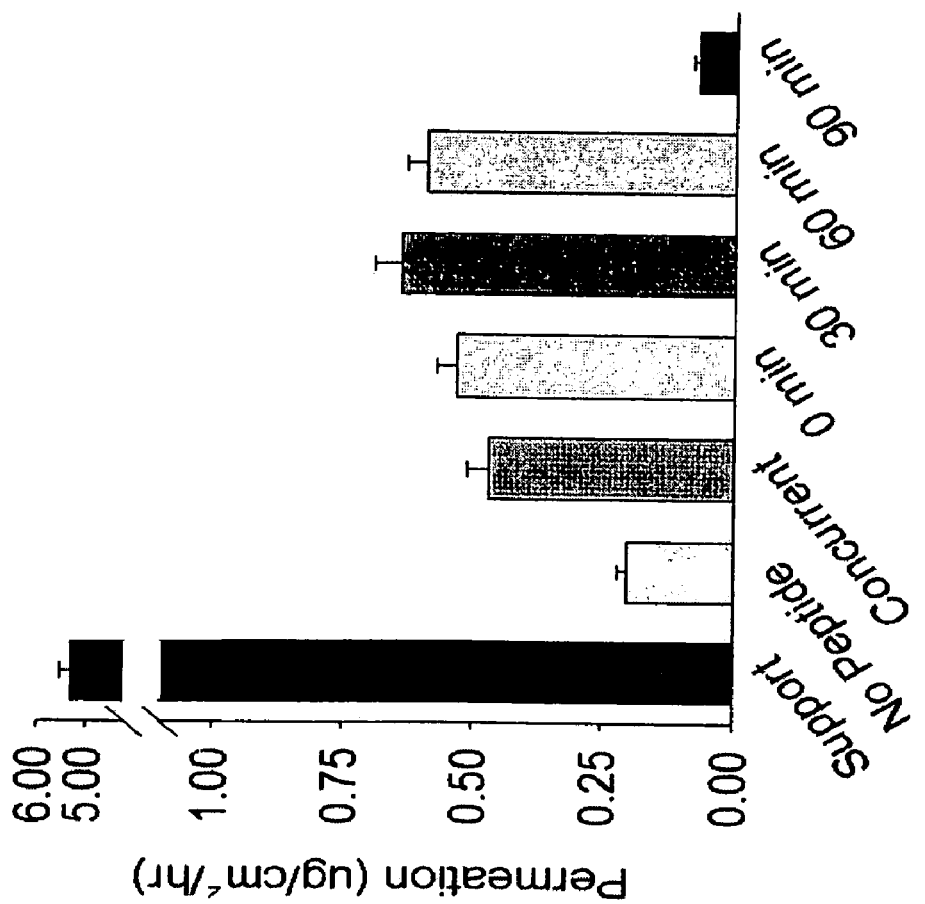
FIG. 8 is a bar graph illustrating peptide-induced permeation of CF in THCE monolayers.

In addition to using rabbit eyes for both in situ and in vivo assays, a corneal cell culture system has been developed for rapid in vitro assays that could reduce the number of test animals that are needed. An SV40-immortalized human corneal epithelial (THCE) cell line grows THCE cells in a defined keratinocyte-SFM medium. Optimally monolayers of the THCE cells should have a transepithelial electrical resistance ($R_{TE}$) greater than 500 $\Omega \cdot cm^2$. Preliminary dextran permeation experiments have shown that at least 70 kDa molecules are able to cross this cultured corneal epithelium after treatment with NC-1059 (Seq. ID No. 1). The paracellular translocation of CF was measured in THCE monolayers grown to confluence on Transwell® supports (FIG. 8). Media was replaced with phosphate buffered saline 60 minutes prior to assay and cells were allowed to acclimate in the incubator. At time=0, the 'concurrent' and the '0, 30, 60, and 90 minute' wells were exposed apically to 100 µM NC-1059 (Seq. ID No. 1). Carboxyfluorescein was added simultaneously to the apical compartment of the 'support, no peptide and concurrent' wells. After 5 minutes of exposure to NC 1059 (Seq. ID No. 1), the apical solution of the 0, 30, 60, and 90 minute wells was replaced with PBS and carboxyfluorescein was immediately added to the '0 minute' well. After 30, 60, and 90 minutes, carboxyfluorescein was added to the apical compartment of the respectively labeled wells. In each case, after 60 minutes of apical exposure to carboxyfluorescein, the basolateral medium was removed to quantify the amount of translocated carboxyfluorescein. Results are summarized from 4 protocols employing tightly paired sets of monolayers. Results indicate that carboxyfluorescein permeation following a five-minute NC-1059 (Seq. ID No. 1) exposure is maximal between 30 and 90 minutes post exposure. After 60 minutes the junctions are beginning to close and by 90 minutes they appear completely resealed. These results are consistent with that observed in the rabbit in vivo studies and suggest that these cells are a suitable corneal model for studying the effects of the peptide.

Figure 9:
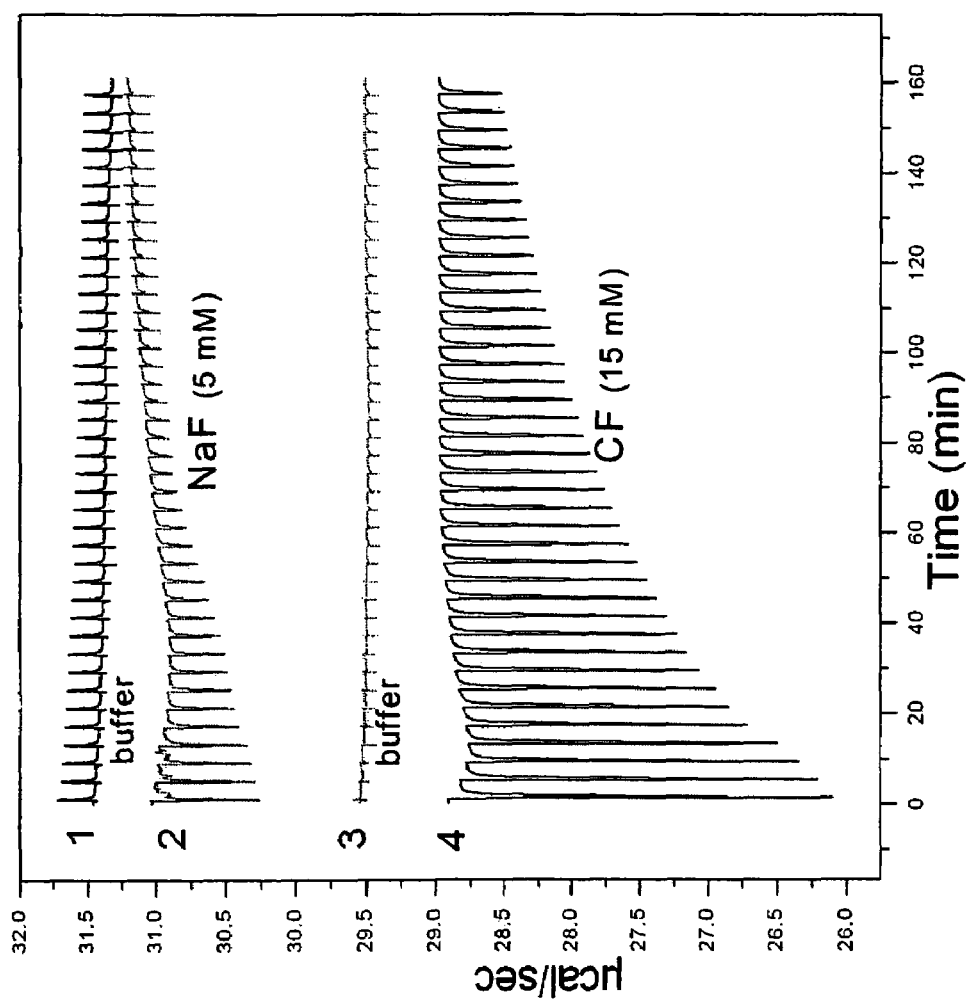
FIG. 9 is a set of isothermal calorimetery plots for buffer, 5 mM NaF and 15 mM CF.

Quantitative isothermal calorimetry experiments were completed for the binding of NaF and CF to NC-1059 (FIG. 9). The interaction is present with both dyes, however CF is greatly reduced compared to that of NaF. Higher dye concentrations were required to see the binding of CF. NaF reaches equilibrium, while CF never does. After subtracting the buffer heats of dilution and plotting the ΔH of injectant vs the molar ratio of dye/peptide, the CF curve is best fit modeling a single binding site while the NaF is best fit to a two-site model. CF, although more hydrophilic, has just one carboxylate while NaF has two sodium hydroxylate groups that can bind to the positively charged lysine groups at the N-terminus.

Example 2

This example will follow the procedures set forth in Example 1, however, conjunctiva-sclera, rather than cornea, will be tested. The tests will use a piece of sclera 16 mm in diameter excised from both globes. The sclera will be obtained from eyes enucleated from euthanized rabbits and will be from an area where there is no muscle attachments or blood vessel leaks as determined with Evans blue stain. For the permeability portion of the assays, the sclera will be clamped in the corneal holder similarly to how the cornea was clamped. The exposed surface area for diffusion was 1.2 $cm^2$ for the cornea and will be 1.1 $cm^2$ for the sclera. The excised conjunctiva-sclera will be mounted choroid side down in a specially designed Lucite perfusion chamber, in which the sclera is mounted horizontally in a two-chambered diffusion apparatus. The diffusion apparatus will be surrounded by a water-circulating jacket connected to a temperature-controlled water bath, that maintains the conjunctiva-sclera and chamber solutions at 37° C. The two chambers will be separated by a double-ring clamp that supports a 1.1 $cm^2$ area of scleral tissue mounted on a corneal ring. The clamp system will be constructed of the same material as the perfusion blocks. Silicone grease (Dow Corning, Midland, Mich.) will be used to create a water-tight seal around the periphery of the clamp, at the junction of the chamber and the clamp.

The conjunctiva-sclera will be clamped between 2.5-mm-wide (and approximately 1-mm-thick) cylindrical rings (Sylgard; Dow Corning, Midland, Mich.) cut to the size of the chamber opening to prevent lateral leakage and scleral edge damage. Chambers with a 7-mm aperture will be used. BSS Plus (Alcon Laboratories, Fort Worth, Tex.) will be perfused through the lower hemichamber (500 μL volume) at a rate of 0.03 ml/min. Fluid mixing will be achieved in the lower hemichamber with a magnetic microstir bar, with the chamber resting on a magnetic stir plate. The tissue will be perfused for 15 to 30 minutes to verify that no leaks are present before applying a test compound to the surface. The test formulations will be adjusted to a total volume of 100 μL with BSS Plus added to the episcleral surface 15 to 30 minutes after the conjunctiva-sclera is mounted in the chamber. The upper hemichamber containing the test compound will be covered with parafilm and seated with silicone grease (Dow coming) along the edges of the exposed area of the chamber to prevent evaporation. This will provide a flexible seal that does not alter transscleral pressure. The temperature of the water-jacketed perfusion chamber will be maintained at 37° C.

Permeability to the fluorescent dye conjugated antibiotics diluted in BSS Plus will be evaluated. The perfusate will be passed through a flow-through quartz cuvete (NSG Precision Cells, Farmingdale, N.Y.), and measurements of total fluorescence in the cuvette will be taken at 60-second intervals using a spectroflourometer (Photon Technology, New Brunswick, N.J.). Time-based fluorescence concentration will be calculated using a standard dilution curve generated from a sample of the donor solution for each experiment. Separate experiments will be performed at transscleral pressures of 0, 15, 30, or 60 mm Hg. Pressure will be applied across the tissue and the outflow tube as it flows into the collector receptacle (e.g., 15 mm Hg will be equivalent to a 22-cm water column). The pressure across the tissue will be verified using a pressure transducer (Statham, Oxnard, Calif.) connected to the lower hemichamber.

Steady state permeability constant ($K_{trans}$) will be calculated from the spectrofluorometry data as: $K_{trans} = R_{total}/(t)(A) \times 1[D]$ where $R_{total}$ is the total amount of drug in the receiver effluent per collected fraction (measured fluorescence units), and t is the fraction collection time (in seconds). A is the area of exposed conjunctiva-sclera (in square centimeters). The value—$R_{total}/(t)(A)$—is equal to the flux across the tissue. D is the concentration of drug in the donor hemichamber (fluorescence units per second per cubic centimeters). Permeability thus represents the steady state flux normalized by donor concentration. The area of exposed sclera will be 0.385 cm$^2$ for the 7-mm chamber and 0.785 cm$^2$ for the 10-mm chamber. Mean permeability values (±SD) will be calculated from three to eight experiments at each pressure in the sclera. Analysis of variance (ANOVA) will be calculated to compare the permeabilities at different pressures for each compound in the sclera. Turkey-Kramer multiple comparisons will then be used to compare differences between pairs of pressure-dependent permeability measurements of each compound in rabbit sclera.

Example 3

This example followed the procedures of the monolayer experiments of Example 1 in order to test the uptake of fluorescently labeled methotrexate (MTX) and MTX that was not fluorescently labeled. Enhanced uptake of the fluorescently labeld MTX was not observed during co-incubation due to adverse interactions between the peptide and the modified drugs. However, in peptide washout experiments in culture, MTX uptake increased by ten-fold. Measurement of the unlabeled MTX was performed using LC-ESI-MS and a standard MTX amount for calibration and comparison purposes.

We claim:

1. A preparation for treatment of ocular tissue and comprising respective amounts of a drug and a peptide, selected from the group consisting of SED ID NO:2, for increasing the transport of the drug through the tissue, as compared with transport of the drug in the absence of the peptide, selected from the group consisting of Emidine, Patanol, Azopt, Ciloxan, Travatan, Aldox, Icaps, Scipro, Hc Otic, Lunigan, Ocu Flox, Cosopt, Timoptic, Allergan's Alphagan, vancomycin, penicillin, dexamethazone, methotrexate, ascorbic acid, benzylpenicillin, tamoxifen, dextran, polymyxin B, BIDPY-vancomycin, neomycin, and mixtures thereof.

2. A method of treating ocular tissue in need thereof comprising the step of contacting said tissue with a preparation as set forth in claim 1, thereby increasing the transport of the drug through the tissue, as compared with transport of the drug in the absence of the peptide.

3. The method of claim 1, said peptide selected from the group consisting of SEQ. ID NO. 2.

4. The method of claim 1, said peptide and drug being in the form of a mixture.

5. The method of claim 4, said mixture including an additional ingredient selected from the group consisting of an acrylic polymer, a buffer, and combinations thereof.

6. The method of claim 1, said peptide and drug being separately contacted with said ocular tissue.

7. The method of claim 1, said peptide and drug being substantially simultaneously contacted with said ocular tissue.

8. The method of claim 1, said peptide and drug being administered within about 2 hours of each other.

9. The method of claim 4, said peptide being present in said mixture at a level of from about 50-500 µM.

10. The method of claim 9, said level being from about 100-300 µM.

11. The method of claim 1, said tissue being corneal or sclera tissue.

12. The method of claim 1, said drug selected from the group consisting of Emidine, Patanol, Azopt, Ciloxan, Travatan, Aldox, Icaps, Scipro, Hc Otic, Lunigan, Ocu Flox, Cosopl, Timoptic, Aiiergan's Alphagan, vancomycin, penicillin, dexamethazone, methotrexate, ascorbic acid, benzylpenecillin, tamoxifen, dextran, polymyxin B, BIDPY-vancomycin, neomycin, and mixtures thereof.

13. The method of claim 4, said drug being present in said mixture at a level of from about 0.05-1000 µM.

14. The method of claim 1, including the step of contacting said drug and peptide with human ocular tissue either in vivo or ex vivo.

15. The method of claim 1, said drug having a molecular weight of at least 70,000 but not greater than 1,500,000.

16. The preparation of claim 1, said preparation comprising a mixture of said drug and said peptide.

17. The preparation of claim 16, said mixture including an additional ingredient selected from the group consisting of an acrylic polymer, a buffer, and combinations thereof.

18. The preparation of claim 1, said peptide being present in said mixture at a level of from about 50-500 µM.

19. The preparation of claim 1, said drug being present in said mixture at a level of from about 0.05-1 000 µM.

20. The preparation of claim 1, said drug having a molecular weight of at least 70,000 but not greater than 1,500,000.

* * * * *

SEQUENCE LISTING

<160> NUMBER OF SEQ ID NOS: 2

<210> SEQ ID NO 1
<211> LENGTH: 27
<212> TYPE: PRT
<213> ORGANISM: Artificial Sequence
<220> FEATURE:
<223> OTHER INFORMATION: Synthetically derived channel-forming peptides

<400> SEQUENCE: 1

Lys Lys Lys Lys Ala Ala Arg Val Gly Leu Gly Ile Thr Thr Val Leu
1               5                   10                  15

Val Thr Thr Ile Gly Leu Gly Val Arg Ala Ala
        20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetically derived channel-forming peptides

<400> SEQUENCE: 2

Lys Lys Lys Lys Val Thr Thr Ile Gly Leu Gly Val Arg Ala Ala Leu
1               5                   10                  15

Ala Ala Arg Val Gly Leu Val Ile Thr Thr Val
        20                  25